United States Patent [19]

DeRidder

[11] Patent Number: 5,509,891

[45] Date of Patent: Apr. 23, 1996

[54] PROTHESIS FOR MALE DYSFUNCTION

[76] Inventor: Paul A. DeRidder, 1125 E. 17th. St., Santa Ana, Calif. 92701

[21] Appl. No.: 358,695

[22] Filed: Dec. 19, 1994

[51] Int. Cl.⁶ ..................................................... A61F 5/41
[52] U.S. Cl. .................................... 600/39; 600/38
[58] Field of Search .................................... 128/842–844, 128/918; 600/38, 39, 41

[56] References Cited

U.S. PATENT DOCUMENTS

| | | | |
|---|---|---|---|
| 844,798 | 2/1907 | Hawley | 600/39 |
| 3,759,254 | 9/1973 | Clark | 600/39 |
| 3,982,530 | 9/1976 | Storch | 600/39 |
| 4,224,933 | 9/1980 | Reiling | 600/39 |
| 4,432,357 | 2/1984 | Pomeranz | 128/844 X |
| 4,895,140 | 1/1990 | Bellak | 600/39 |
| 4,899,737 | 2/1990 | Lazarian | 600/39 |

FOREIGN PATENT DOCUMENTS 385665 12/1922 Germany ..................... 600/41

*Primary Examiner*—Angela D. Sykes
*Assistant Examiner*—Samuel Gilbert
*Attorney, Agent, or Firm*—Plante & Strauss

[57] ABSTRACT

There disclosed a prothesis for male erectile dysfunction. The prothesis comprises a sheath, quite similar in size and thickness to a conventional condom which has at least two longitudinal retractable stiffeners embedded within said sheath and oriented so that the stiffener has a stable coiled configuration and a stable extended configuration. The stiffeners are formed of thin, elastic sheet material which can be rolled into a coil, and which readily unrolls. At least two stiffeners are provided, extending longitudinally along the extended sheath configuration and these are spaced apart by an angular increment which is sufficient to maintain the sheath in its extended configuration. The material of the sheath is sufficiently elastic to permit the stiffener to be roll and unrolled.

16 Claims, 2 Drawing Sheets

PROTHESIS FOR MALE DYSFUNCTION

BACKGROUND OF THE INVENTION

1. Field of Invention

This invention relates to a prothesis for male erectile dysfunction, and in particular, to a condom with penile supporting splint members.

2. Brief Statement of the Prior Art

Various penile prosthesis have been provided, including complex implants which are extendible by transferring of inflation fluid from a sack to a tubular implant in the penis. These complex penile implants are costly and subject the patient to an operation for implanting the prosthesis, and a second operation should it be desired or necessary to remove the implant.

U.S. Pat. No. 4,895,140 discloses a prosthesis formed of filaments which are oriented in longitudinal, circular and helical directions and interwoven into a sheath.

U.S. Pat. No. 4,224,933 discloses a sexual stabilizer and stimulator which has a tubular body formed of latex with five to seven stays 18 embedded within the latex body.

U.S. Pat. No. 4,899,737 discloses a splint for complete circumferential immobilization of an extremity. The splint is a cylindrical rubber-like tubing in which are embedded a plurality of rod-like stiffening members 16, which may be formed of steel.

U.S. Pat. No. 3,131,691 discloses a surgical splint having a cradle and a strut which are integrally coupled at opposing ends by tubular webs 4 and 5.

U.S. Pat. No. 3,759,254 discloses a condom having a relatively stiff, but flexible, cartilaginous rib which functions as a temporary prosthesis to aid males with erectile dysfunction. U.S. Pat. No. 4,625,716 discloses a condom provided with a plurality of longitudinally extended compartments which are filled with a rheopexic fluid for stiffening the structure and supporting the penis thereby.

The aforementioned splint devices lack one or more desirable features necessary for acceptance of the prothesis. Indeed, some even contradict current medical practice by providing sheaths which totally surround the penis, thereby risking restriction of circulation.

Ideally, the splints should be sufficiently flexible to permit the device to be rolled into a compact configuration readily unrolled at time of use, as a conventional condom. The device should also not numb sensations which would rendering the condom inappropriate for sexual pleasure.

OBJECTIVES OF THE INVENTION

It is an objective of this invention to provide a prothesis for male erectile dysfunction.

It is a further objective of this invention to provide the prothesis as easy to use as a conventional condom.

It is an additional objective of this invention to provide the prothesis as a condom with support members which can be rolled and unrolled as a condom.

It is also an objective of this invention to provide the prothesis with support members which do not inhibit the pleasurable and sensation of practice of the sexual act.

Other and related objectives will be apparent from the following description of the invention.

BRIEF STATEMENT OF THE INVENTION

This invention comprises a prothesis for male erectile dysfunction. The prothesis comprises a sheath, quite similar in size and thickness to a conventional condom which has at least two longitudinal retractable stiffeners embedded within said sheath and oriented so that the stiffener has a stable coiled configuration and a stable extended configuration. The stiffeners are formed of thin, elastic sheet material which can be rolled into a coil, and which readily unrolls. At least two stiffeners are provided, extending longitudinally along the extended sheath configuration and these are spaced apart by an angular increment which is sufficient to maintain the sheath in its extended configuration. The material of the sheath is sufficiently elastic to permit the stiffener to be roll and unrolled.

BRIEF DESCRIPTION OF THE DRAWINGS

The invention will be described with reference to the figures, of which.

DESCRIPTION OF THE PREFERRED EMBODIMENT

Figure 1:
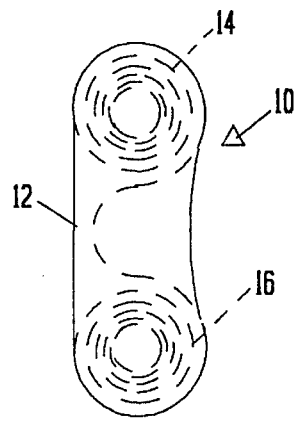
FIG. 1 is a view of the prosthesis in its rolled or compact configuration.

The prothesis 10 of the invention is shown in FIG. 1 in its rolled or compact configuration, similar to a condom prior to application. The prothesis 10 has a thin film sheath 12 formed of an elastomer, preferably of latex rubber which has a thickness from about 0.2 to about 2 millimeters.

Unlike conventional condoms, however, the prothesis has a pair of coiled stiffeners 14 and 16, which are entirely embedded within the thin film sheath 12. The stiffeners can be located about the sheath at an angular incremental spacing from about 30° to about 180°, which is sufficient to provide rigidity to the extended configuration. It is apparent that rolling of the sheath and stiffeners requires that the material of the sheath be stretched, and the greatest stretch being required when the stiffeners 14 and 16 are on opposite sides of the sheath, i.e., at 180° incremental spacing. Alternatively, three of more stiffeners can be used, which also increases the extent of stretching required to roll and unroll the sheath 12.

The stiffeners 14 and 16 can be formed of resilient, spring-like materials, e.g., metal such as stainless steel, titanium, or of plastics such as polyethylene, polyvinyl chloride, polyesters such as Mylar, polyurethanes, etc. The stiffeners 14 and 16 have a greater width than thickness, e.g., have a width from 0.125 to about 0.5 inch, preferably from 0.2 to about 0.4 inch, and a thickness from about 0.01 to about 0.1 inch, so that they are flexible and will bend only substantially only in the direction orthogonal to their thickness, as required to roll them into a coil. The prothesis will stay in the illustrated, rolled configuration as the material of the sheath will resist unrolling, so the prosthesis will retain the compact configuration shown in FIG. 1, once the stiffeners 14 and 16 are rolled into coils.

Figure 2:
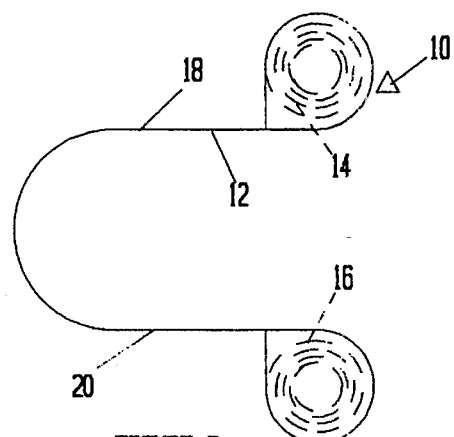
FIG. 2 is a view of the prosthesis as it is unrolled during application.
Figure 4:
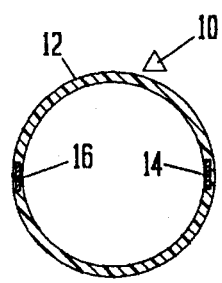
FIG. 4 is a cross sectional view along line 4-4' of FIG. 3.
Figure 3:
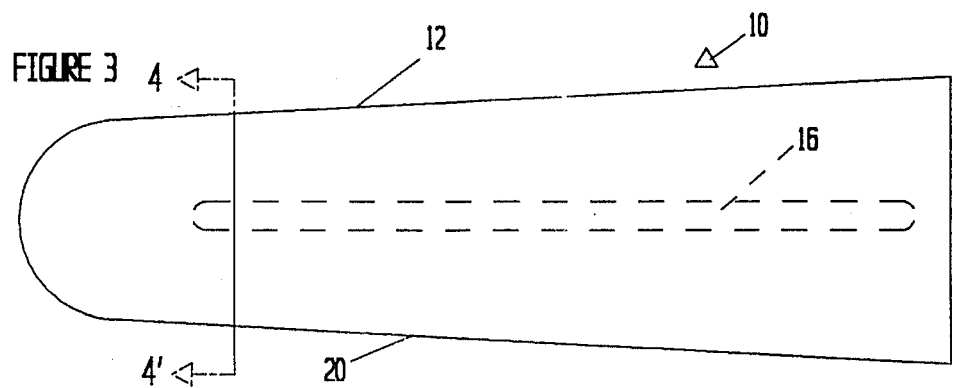
FIG. 3 is a side view of the prothesis in its extended position.

As shown by FIG. 2, the prosthesis 10 is applied by unrolling the sheath 12 over the penis, with the stiffeners 14 and 16 being manually uncoiled. As shown in FIG. 3, each stiffener such as 14 assumes a stable, semi-rigid configuration, in which it will accommodate flexing along its narrow thickness, but will resist flexing arcuate cross section 22. The preferred cross section for the stiffeners is rectangular, as illustrated, however, a slightly arcuate cross-section can also be useful. As apparent from FIG. 4, the stiffener is entirely embedded within the sheath 12 of the prosthesis 10.

FIG. 3 illustrates the prosthesis 10 in its fully extended configuration, in which the stiffeners such as 16 extend along opposite sides of the penis. In this configuration, the stable extended configuration of the stiffeners 14 and 16 support and contribute stiffness to the penis. In the illustrated embodiment, the stiffeners 14 and 16 provide support on opposite sides 18 and 20 of the penis. The stiffeners terminate short of the glans penis, so that stimulation of the more sensitive are of the glans penis is uninhibited by the stiffeners.

Figure 5:
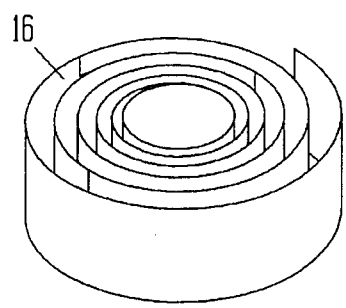
FIG. 5 is a perspective view of a suitable stiffener member in its coiled configuration.

FIG. 5 illustrates the coiled configuration of the stiffener 16, without the sheath 12. As there illustrated, the cross section of the stiffener 16 is flat, or planar. Because of the difficulty of scale, the thickness of the stiffener is minimized in the illustration.

Figure 6:
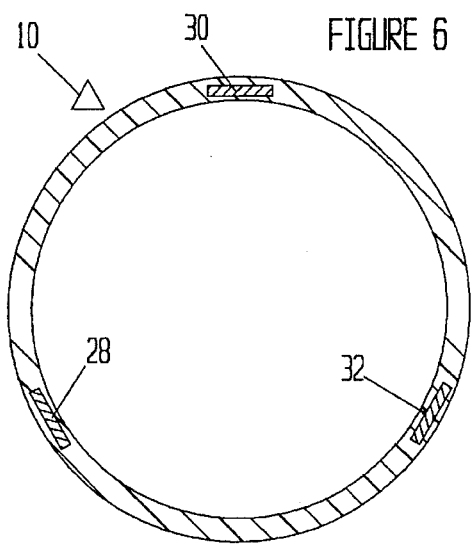
FIG. 6 is cross sectional view of another prosthesis of the invention.

Various alternative forms of the prosthesis can be provided; as shown in FIG. 6, three stiffeners 28, 30 and 32 can be provided, one at each side and one on the top of the prosthesis.

Figure 7:
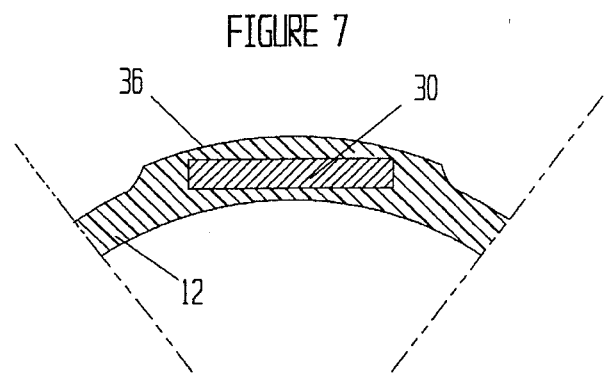
FIG. 7 is a cross sectional view of a prosthesis with stiffeners of the invention in a condom sheath of conventional film thickness.

In some applications, it may be desirable to limit the film thickness of the sheath in the non-reinforced areas. As shown in FIG. 7, this can be accomplished by increasing the sheath thickness only about the stiffeners 30, resulting in the illustrated cross-section in which the thickness of the sheath 12 in the region 36 of the stiffener 30 is from 2 to 5 times greater than the thickness of the film in the other areas 38 of the sheath 12.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims:

What is claimed is:

1. A reinforced form-supporting penile prothesis which comprises:

a. a tubular condom sheath formed of a latex rubber film having a thickness from 0.2 to 2 millimeters; and b. at least two stiffeners, each having a width to thickness ratio from 5 to 20 which extend entirely longitudinally along said tubular condom sheath and parallel to each other, spaced apart by an angular increment from 30° to 180°, and which are embedded with their thickness within the thickness of said film and are formed of thin, flexible sheet material sufficiently flexible and said latex rubber being sufficiently elastic to permit said stiffeners to coil, whereby said prothesis can be rolled and unrolled between stable coiled and stable extended configurations.

2. The penile prothesis of claim 1 wherein said film has a thickness from 0.5 to about 1.5 millimeters.

3. The penile prothesis of claim 1 wherein said stiffeners are formed of metal.

4. The penile prothesis of claim 1 having a pair of said stiffeners disposed at approximately equal circumferential spacings about said penile prothesis.

5. The penile prothesis of claim 1 having three of said stiffeners disposed at approximately equal circumferential spacings about said condom sheath.

6. The penile prothesis of claim 1 wherein said stiffeners are formed of a flexible plastic.

7. The penile prothesis of claim 6 wherein said stiffeners are formed of a thermoplastic resin.

8. The penile prothesis of claim 1 wherein said stiffeners are formed of a polyester.

9. A penile erection prosthesis which comprises:

a. a tubular penile shroud formed of a latex rubber film having a thickness from 0.2 to 2 millimeters;

b. at least two stiffeners disposed longitudinally along said tubular penile shroud and parallel to each other, and embedded with their thickness within said film and spaced apart by an angular increment from 30° to 180°, said stiffeners being formed of thin, flexible material with cross sections having greater width than thickness and being sufficiently flexible and said latex rubber being sufficiently elastic to permit said prothesis to be rolled and unrolled between coiled and extended configurations.

10. The penile erection prosthesis of claim 9 in a rolled-up configuration in which said stiffeners are coiled and said shroud is rolled up on itself.

11. The penile erection prosthesis of claim 1 wherein said film has a thickness from 0.5 to 1.5 millimeters.

12. The penile erection prosthesis of claim 11 wherein said stiffeners are formed of metal.

13. The penile erection prosthesis of claim 11 wherein said shroud has a pair of said stiffeners disposed at approximately equal circumferential spacings about said tubular penile shroud.

14. The penile erection prosthesis of claim 11 wherein said shroud has at least three of said stiffeners disposed at approximately equal circumferential spacings about said tubular penile shroud.

15. The penile erection prosthesis of claim 11 wherein said stiffeners are formed of a thermoplastic resin.

16. The penile erection prosthesis of claim 11 wherein said stiffeners are formed of a polyester.

* * * * *